US011426285B2

(12) United States Patent
Terrill et al.

(10) Patent No.: US 11,426,285 B2
(45) Date of Patent: Aug. 30, 2022

(54) TRUSS GLENOID AUGMENT

(71) Applicant: Howmedica Osteonics Corp., Mahwah, NJ (US)

(72) Inventors: Lance N. Terrill, League City, TX (US); Andrew J. Nelson, New City, NY (US); Garrett Campbell, Huntington, NY (US)

(73) Assignee: Howmedica Osteonics Corp., Mahwah, NJ (US)

(*) Notice: Subject to any disclaimer, the term of this patent is extended or adjusted under 35 U.S.C. 154(b) by 0 days.

(21) Appl. No.: 16/990,155

(22) Filed: Aug. 11, 2020

(65) Prior Publication Data

US 2021/0068968 A1 Mar. 11, 2021

Related U.S. Application Data

(60) Provisional application No. 62/896,057, filed on Sep. 5, 2019.

(51) Int. Cl.
*A61F 2/40* (2006.01)
*A61F 2/24* (2006.01)
(Continued)

(52) U.S. Cl.
CPC .. *A61F 2/4081* (2013.01); *A61F 2002/30125* (2013.01); *A61F 2002/30433* (2013.01);
(Continued)

(58) Field of Classification Search
CPC ...... A61F 2002/2835; A61F 2002/2839; A61F 2002/30736; A61F 2002/30884;
(Continued)

(56) References Cited

U.S. PATENT DOCUMENTS

| 3,559,514 A | 2/1971 | Brownfield |
| 4,828,439 A * | 5/1989 | Giannuzzi ............. F16B 13/061 411/908 |

(Continued)

FOREIGN PATENT DOCUMENTS

| EP | 3378444 A1 | 9/2018 |
| EP | 3403617 A1 | 11/2018 |

OTHER PUBLICATIONS

"Knowles Nikolas K et al. ""Augmented glenoid component designs for type B2 erosions: a computational comparison by volume of bone removal and quality of remaining bone."" Journal of shoulder and elbow surgery vol. 248 (Jan. 31, 2015): 1218-26. doi:10.1016/j.jse.2014.12.018".

(Continued)

*Primary Examiner* — Ann Schillinger
(74) *Attorney, Agent, or Firm* — Lerner, David, Littenberg, Krumholz & Mentlik, LLP

(57) ABSTRACT

According to one aspect of the disclosure, a glenoid implant for replacing a native glenoid includes an articulating surface configured to articulate with respect to a humeral head. A bone-facing surface may be opposite the articulating surface, the bone-facing surface having a first area configured to contact a paleoglenoid of the native glenoid. An augment portion may be coupled to the bone-facing surface, the augment portion being configured to contact a neoglenoid of the native glenoid. The augment portion may be transitionable between a first configuration in which the augment portion has a first convexity and a second configuration in which the augment portion has a second convexity different than the first convexity.

16 Claims, 8 Drawing Sheets

(51) Int. Cl.
*A61F 2/88* (2006.01)
*A61F 2/30* (2006.01)
*A61F 2/91* (2013.01)

(52) U.S. Cl.
CPC ............... *A61F 2310/00023* (2013.01); *A61F 2310/00179* (2013.01)

(58) Field of Classification Search
CPC .... A61F 2/28; A61F 2/30734; A61F 2/30767; A61F 2/34; A61F 2/40; A61F 2/4014; A61F 2/4607; A61F 2002/3021; A61F 2002/30276; A61F 2002/30281; A61F 2/36; A61F 2/3609; A61F 2/3662; A61F 2/3859; A61F 2/3872; A61F 2/4003; A61F 2/4081; A61F 2/4612; A61F 2002/30125; A61F 2002/30433; A61F 2310/00023; A61F 2310/00179; A61F 2/30749
See application file for complete search history.

(56) References Cited

U.S. PATENT DOCUMENTS

| | | | |
|---|---|---|---|
| 5,203,653 A | 4/1993 | Kudla | |
| 5,591,170 A | 1/1997 | Spievack et al. | |
| 5,800,551 A | 9/1998 | Williamson et al. | |
| 5,919,195 A | 7/1999 | Wilson et al. | |
| 6,699,289 B2 | 3/2004 | Iannotti et al. | |
| 6,949,101 B2 | 9/2005 | McCleary et al. | |
| 7,217,271 B2 | 5/2007 | Wolford et al. | |
| 7,473,254 B2 | 1/2009 | White et al. | |
| 7,503,921 B2 | 3/2009 | Berthusen et al. | |
| 7,572,259 B2 | 8/2009 | Desarzens et al. | |
| 7,637,909 B2 | 12/2009 | Lechot et al. | |
| 7,749,227 B2 | 7/2010 | Lechot et al. | |
| 7,780,669 B2 | 8/2010 | Lechot et al. | |
| 7,785,329 B2 | 8/2010 | Lechot et al. | |
| 7,803,160 B2 | 9/2010 | Keller | |
| 7,819,875 B2 | 10/2010 | Chana | |
| 7,892,287 B2 | 2/2011 | Deffenbaugh | |
| 7,922,769 B2 | 4/2011 | Deffenbaugh et al. | |
| 7,927,335 B2 | 4/2011 | Deffenbaugh et al. | |
| 7,993,408 B2 | 8/2011 | Meridew et al. | |
| 8,052,690 B2 | 11/2011 | Berthusen et al. | |
| 8,282,639 B2 | 10/2012 | Chana | |
| 8,475,460 B1 | 7/2013 | Roger et al. | |
| 8,480,674 B1 | 7/2013 | Roger et al. | |
| 8,486,076 B2 | 7/2013 | Chavarria et al. | |
| 8,657,833 B2 | 2/2014 | Burgi et al. | |
| 8,657,834 B2 | 2/2014 | Burgi | |
| 8,721,727 B2 | 5/2014 | Ratron et al. | |
| 8,740,907 B2 | 6/2014 | Penenberg | |
| 8,771,275 B2 | 7/2014 | Xie et al. | |
| 8,864,834 B2 | 10/2014 | Boileau et al. | |
| 9,066,730 B2 | 6/2015 | McMinn et al. | |
| 9,066,731 B2 | 6/2015 | Moore | |
| 9,078,672 B1 | 7/2015 | Rosse | |
| 9,408,652 B2 | 8/2016 | Hassler et al. | |
| 9,414,927 B2 | 8/2016 | Iannotti et al. | |
| 10,028,838 B2 | 7/2018 | Hodorek et al. | |
| 2003/0163135 A1 | 8/2003 | Hathaway | |
| 2003/0220646 A1 | 11/2003 | Thelen et al. | |
| 2004/0097947 A1 | 5/2004 | Wolford et al. | |
| 2004/0133275 A1* | 7/2004 | Mansmann | A61F 2/30965 623/23.51 |
| 2004/0236339 A1 | 11/2004 | Pepper | |
| 2005/0159751 A1 | 7/2005 | Berthusen et al. | |
| 2005/0234460 A1* | 10/2005 | Miller | A61F 2/0811 606/232 |
| 2006/0015110 A1 | 1/2006 | Pepper | |
| 2006/0058809 A1 | 3/2006 | Zink et al. | |
| 2006/0074421 A1* | 4/2006 | Bickley | A61B 17/686 606/291 |
| 2007/0038302 A1 | 2/2007 | Shultz et al. | |
| 2007/0038303 A1 | 2/2007 | Myerson et al. | |
| 2007/0093840 A1 | 4/2007 | Pacelli et al. | |
| 2008/0021474 A1* | 1/2008 | Bonutti | A61B 17/8863 606/28 |
| 2008/0027441 A1* | 1/2008 | Lopez | A61F 2/0811 606/916 |
| 2009/0270863 A1 | 10/2009 | Maisonneuve | |
| 2010/0228352 A1 | 9/2010 | Courtney, Jr. et al. | |
| 2011/0004215 A1 | 1/2011 | Bradley et al. | |
| 2012/0109229 A1 | 5/2012 | Forsell | |
| 2012/0123419 A1 | 5/2012 | Purdy et al. | |
| 2012/0239042 A1 | 9/2012 | Lappin et al. | |
| 2013/0053891 A1* | 2/2013 | Hawkins | A61F 2/4611 606/264 |
| 2013/0090737 A1* | 4/2013 | Flaherty | A61F 2/30749 623/19.13 |
| 2013/0123930 A1* | 5/2013 | Burt | A61F 2/4003 623/19.14 |
| 2013/0144393 A1 | 6/2013 | Mutchler et al. | |
| 2013/0216297 A1* | 8/2013 | Albach | F16B 21/075 403/20 |
| 2014/0128983 A1* | 5/2014 | Flaherty | A61B 17/842 623/19.13 |
| 2014/0277518 A1* | 9/2014 | Iannotti | A61F 2/4081 623/19.11 |
| 2016/0310285 A1 | 10/2016 | Kovacs et al. | |
| 2018/0021050 A1* | 1/2018 | Little | A61B 17/8057 606/280 |
| 2018/0318110 A1* | 11/2018 | Bushell | A61F 2/34 |
| 2019/0151106 A1 | 5/2019 | Kovacs et al. | |
| 2021/0228372 A1* | 7/2021 | Knox | A61F 2/4612 |
| 2021/0401584 A1* | 12/2021 | Gargac | A61F 2/30771 |

OTHER PUBLICATIONS

Karelse, Anne, et al. "Rocking-horse phenomenon of the glenoid component: the importance of inclination." Journal of Shoulder and Elbow Surgery 24.7 (Mar. 11, 2015): 1142-1148.

Knowles, N. K., Ferreira, L. M., & Athwal, G. S. (Jan. 23, 2016). The arthritic glenoid: anatomy and arthroplasty designs. Current reviews in musculoskeletal medicine, 9(1), 23-29. <https://doi.org/10.1007/s12178-016-9314-2>.

Knowles, Nikolas K., "Osteoarthritis Induced Glenoid Morphology and Bone Quality: An Evaluation of Augmented Glenoid Components", Apr. 15, 2015, Electronic Thesis and Dissertation Repository. 2752, 172 pages, <https://ir.lib.uwo.ca/etd/2752>.

Mcguire, DT, Vrettos, B, Roche, S, & Walters, J. (Jan. 2012). Bone loss in shoulder replacement surgery: a review of current management. SA Orthopaedic Journal, 11(3), 47-55. Retrieved Jul. 9, 2020, from <http://www.scielo.org.za/scielo.php?script=sci_arttext&pid=S1681-150X2012000300005&lng=en&tlng=en>.

Extended European Search Report including Written Opinion for Application No. EP20194646.4, dated Feb. 1, 2021, pp. 1-5.

* cited by examiner

TRUSS GLENOID AUGMENT

CROSS-REFERENCE TO RELATED APPLICATIONS

This application claims the benefit of the filing date of U.S. Provisional Patent Application No. 62/896,057, filed Sep. 5, 2019, the disclosure of which is hereby incorporated by reference herein.

BACKGROUND OF THE DISCLOSURE

Eccentric glenoid erosion may occur in as many as 40% of shoulder arthroplasty candidates. Wear can present anteriorly, superiorly and posteriorly, with superior being most common in reverse shoulder arthroplasty ("RSA") candidates, and posterior being most prevalent in total shoulder arthroplasty ("TSA") candidates. As the articular surface of the glenoid wears or degrades over time, the glenoid surface may take a biconcave shape (for example, a Walch B2 classification). The worn or degraded portion of the glenoid may be referred to as the neoglenoid and the original portion of the glenoid may be referred to as the paleoglenoid. As the neoglenoid surface develops, it may begin to form a pseudo-articular surface that has cortical-type bone.

Any glenoid implant that does not have a bone-contacting surface design (such as a bi-convex design) to match the corresponding surface(s) of a glenoid with eccentric glenoid erosion may require removal of a relatively large amount of bone stock, including portions of the paleoglenoid, which may be undesirable. Preferably, prostheses that are designed to fit the neoglenoid should closely approximate the surface of both the neoglenoid and the paleoglenoid to be able to most effectively transfer stress to the bone in as close a manner as possible to the pre-operative state.

As eccentric glenoid erosion progresses, the relative sizes and shapes of the paleoglenoid and the neoglenoid may also change. It would thus be preferably to have an augmented glenoid implant that is capable of being implanted onto a glenoid with eccentric glenoid erosion to minimize the amount of native bone stock that needs to be removed. In addition, it would be preferable to have an augmented glenoid implant or implant system that performs well when implanted onto a native glenoid with eccentric glenoid erosion. It would additionally be preferable to have an augmented glenoid implant or implant system that is suitable for use in patients with different progressions of eccentric glenoid erosion. For example, glenoid implants with augments are typically only offered in one size, or a few discrete sizes. For such offerings, intraoperative adjustment of the implant is not possible, and a poor fit with the bone may result.

BRIEF SUMMARY

According to one aspect of the disclosure, a glenoid implant for replacing a native glenoid includes an articulating surface configured to articulate with respect to a humeral head. A bone-facing surface may be opposite the articulating surface, the bone-facing surface having a first area configured to contact a paleoglenoid of the native glenoid. An augment portion may be coupled to the bone-facing surface, the augment portion being configured to contact a neoglenoid of the native glenoid. The augment portion may be transitionable between a first configuration in which the augment portion has a first convexity and a second configuration in which the augment portion has a second convexity different than the first convexity. The augment portion may have a first end coupled to the bone-facing surface, and a second free end, the second free end being movable with respect to the bone-facing surface. The augment portion may include a plurality of beams, each beam having a first end coupled to the bone-facing surface, and a second end coupled to a rim, the rim connecting the second ends of the beams. The rim may include two terminal ends coupled to the bone-facing surface. The plurality of beams may include three beams. The rim may have a contour that matches a contour of a posterior perimeter of the bone-facing surface. A plurality of fastener apertures may be in the bone-facing surface, each fastener aperture configured to receive a fastener therethrough. At least one of the fastener apertures may have a longitudinal axis that extends between two adjacent beams of the plurality of beams.

A set screw aperture may be positioned in the bone-facing surface, the set screw aperture configured to receive a set screw therethrough. The set screw aperture may have a longitudinal axis that aligns with a corresponding one of the plurality of beams. The glenoid implant may include the set screw. The set screw may have threads, and the set screw aperture may have corresponding threads. The set screw is configured to be advanced through the set screw aperture so that a leading end of the set screw contacts the corresponding one of the plurality of beams. The first ends of the plurality of beams may be positioned along a transition line. The bone-facing surface may have a second area configured to be spaced away from the paleoglenoid of the native glenoid, the first area and the second area of the bone-facing surface being separated by the transition line. The glenoid implant may include a base and an articulation portion adapted to couple to the base. The bone-facing surface may be positioned on the base, and the articulating surface may be positioned on the articulation portion.

According to another aspect of the disclosure, a method of implanting a glenoid implant onto a native glenoid of a patient may include transitioning an augment portion from a first configuration in which the augment portion has a first convexity to a second configuration in which the augment portion has a second convexity different than the first convexity. The augment portion may be coupled to a bone-facing surface of the glenoid implant. The glenoid implant may be fixed to the native glenoid so that the augment portion confronts a neoglenoid of the native glenoid while in the second configuration, and a first area of the bone-facing surface confronts a paleoglenoid of the native glenoid, and so that an articulating surface of the glenoid implant opposite the bone-facing surface is positioned to articulate with respect to a humeral head of the patient. The augment portion may be transitioned from the first configuration to the second configuration prior to the glenoid implant being fixed to the native glenoid. The augment portion may be transitioned from the first configuration to the second configuration while the glenoid implant is at least partially fixed to the native glenoid. Transitioning the augment portion from the first configuration to the second configuration may include driving a set screw through a set screw aperture in the bone-facing surface until a tip of the set screw contacts a first beam of the augment portion causing the augment portion to at least partially move away from the bone-facing surface of the glenoid implant. The augment portion may include peripheral beams and a rim, the first beam being positioned between the peripheral beams, the first beam and the peripheral beams all having first ends coupled to the bone-facing surface, and second ends coupled to the rim.

DETAILED DESCRIPTION

When referring to specific directions in the following discussion of certain implantable joint replacement devices, it should be understood that such directions are described with regard to the orientation and position of the implantable joint replacement devices during exemplary application to the human body in an intended position and/or orientation. Thus, as used herein, the term "proximal" means situated relatively close to the heart of the body and the term "distal" means situated relatively far from the heart. The term "anterior" means towards the front part of the body (or the face) and the term "posterior" means towards the rear of the body. The term "medial" means toward the midline of the body and the term "lateral" means away from the midline of the body. Further, as used herein, the terms "about," "generally," and "substantially" are intended to mean deviations from absolute are included within the scope of the term so modified.

Figure 1:
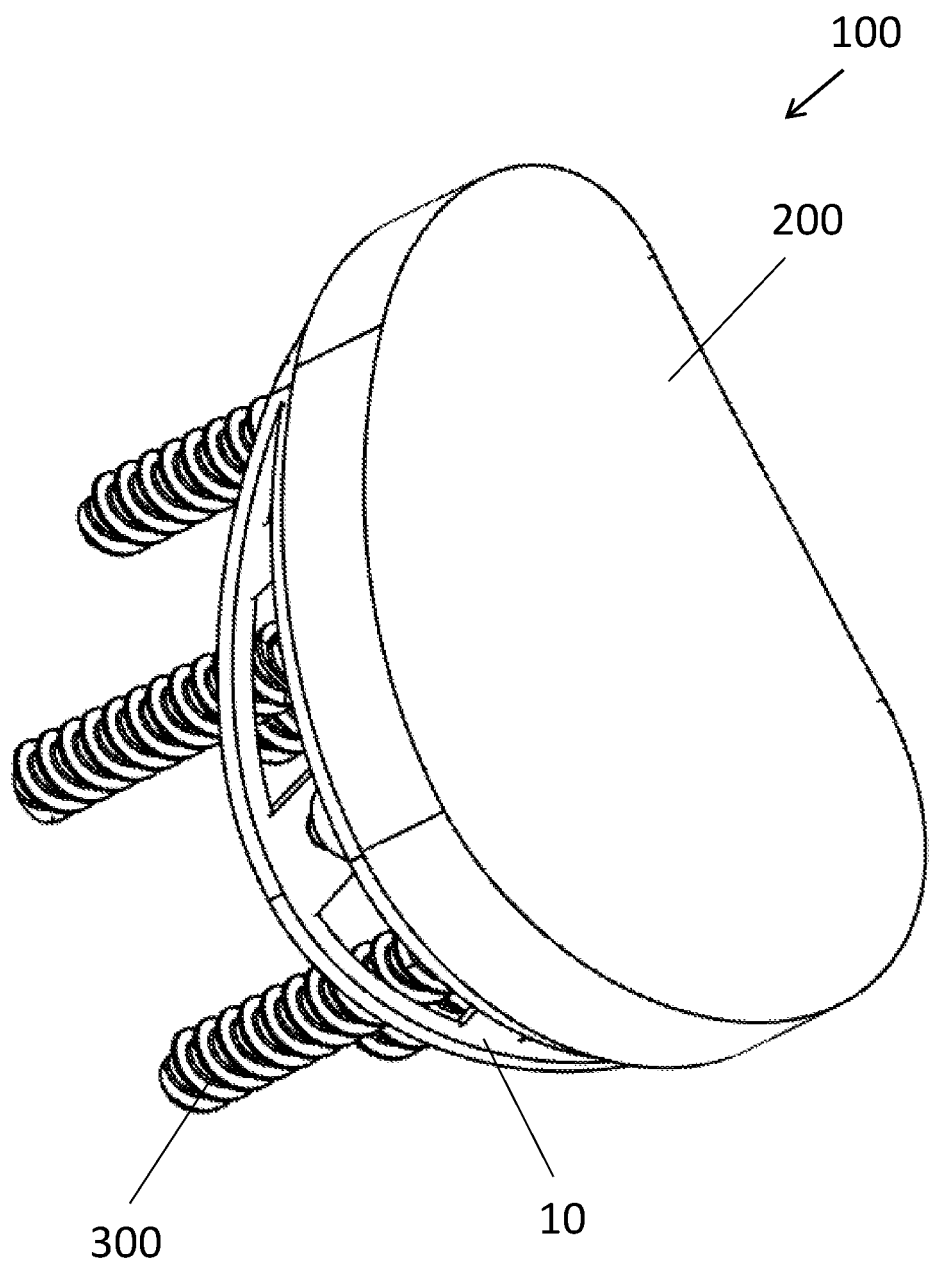
FIGS. 1 and 2 are perspective views of an augmented glenoid implant
Figure 2:
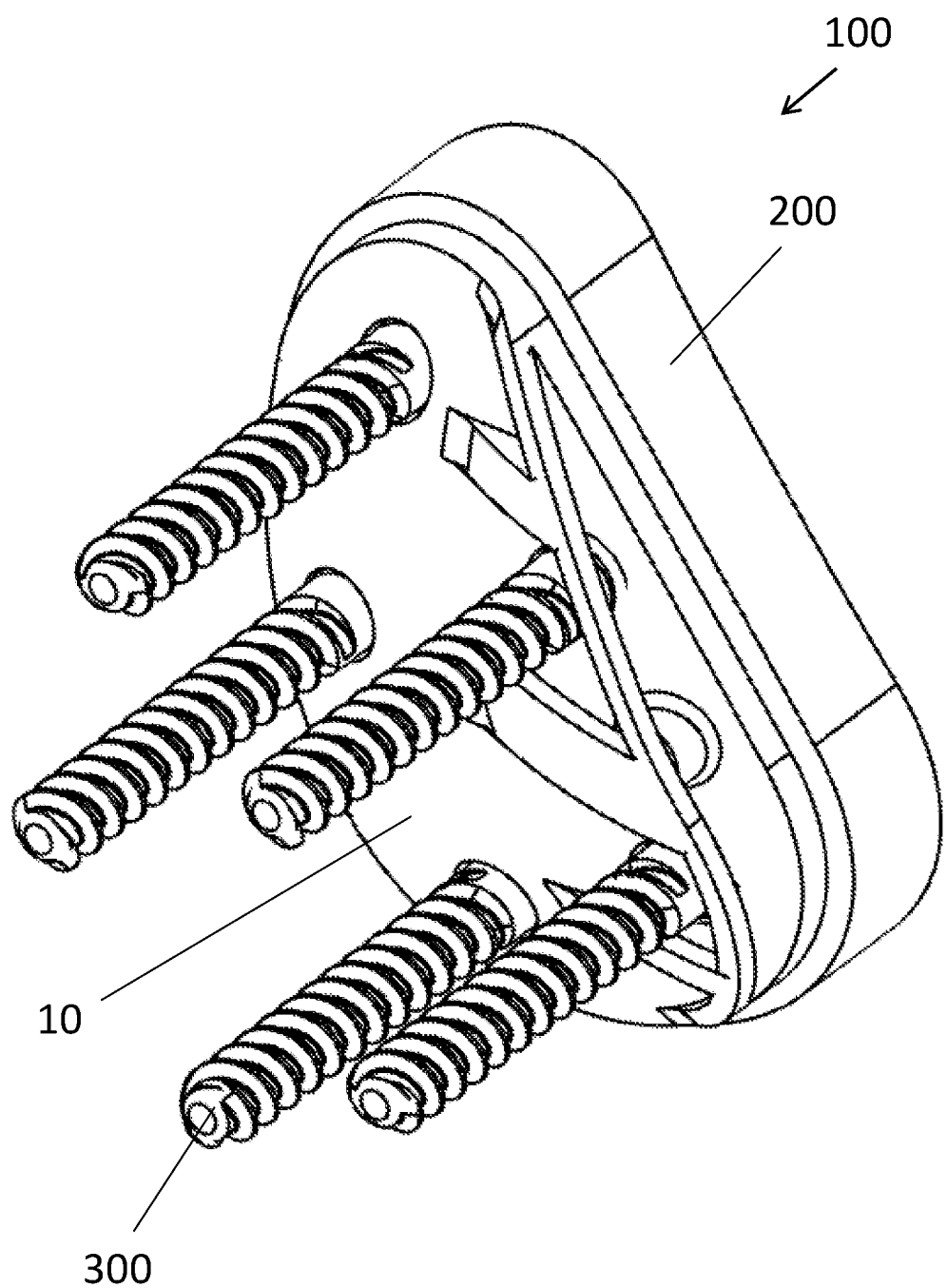
Figure 3:
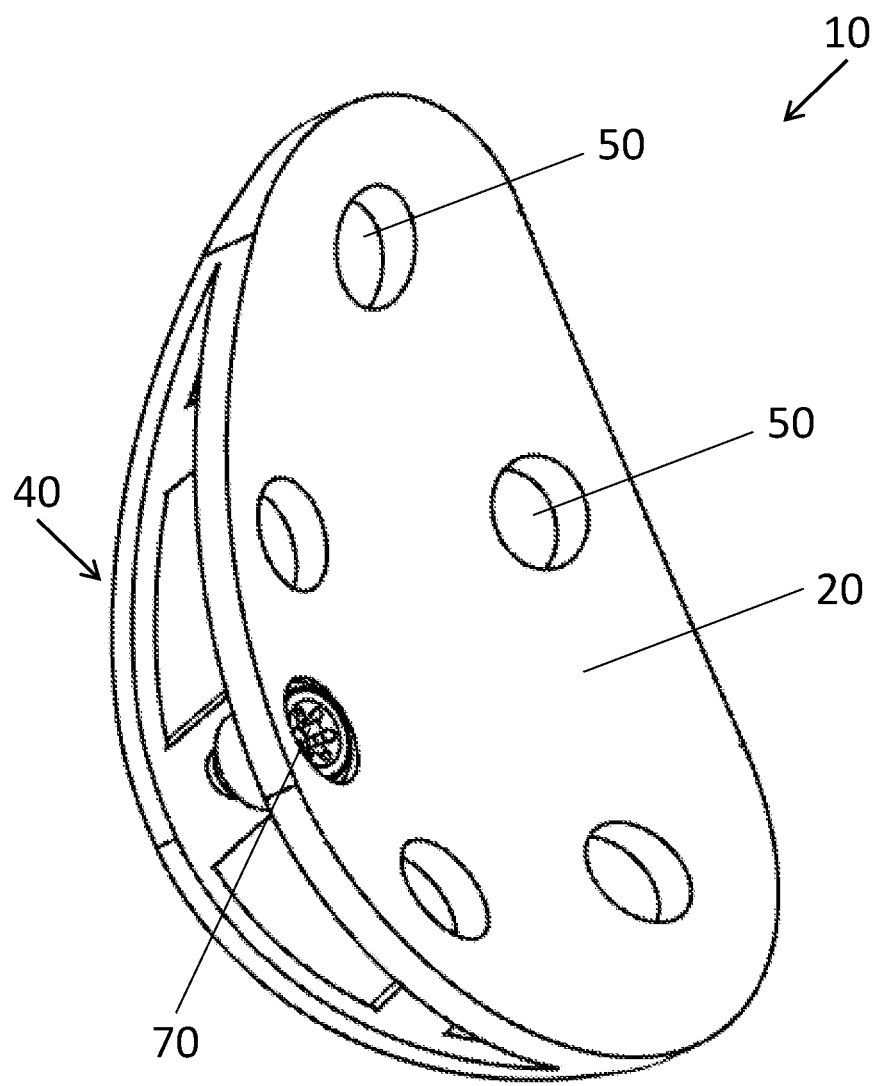
FIG. 3 is a perspective view of a base of the augmented glenoid implant of FIG. 1.
Figure 4:
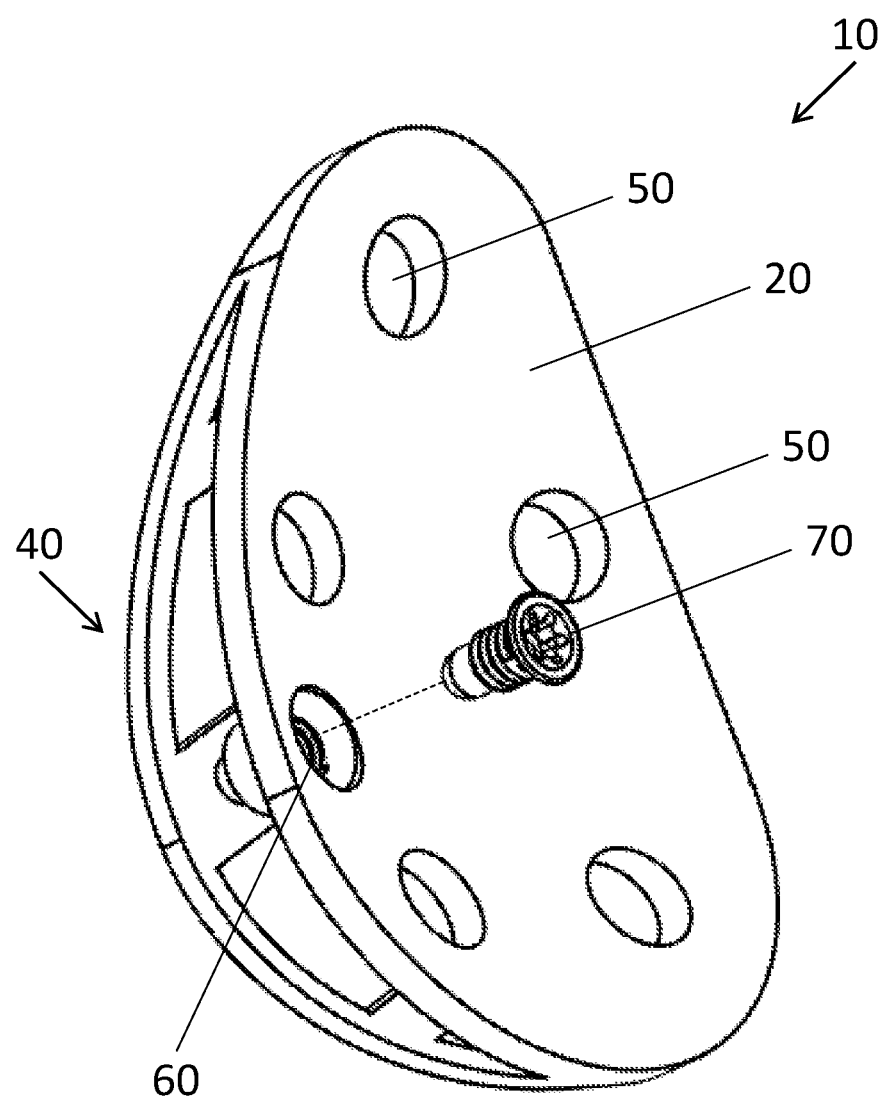
FIG. 4 is an exploded perspective view of the base of FIG. 3.

FIGS. 1 and 2 are perspective views of a right glenoid implant 100 according to an aspect of the disclosure. It should be understood that a left glenoid implant may be provided that is substantially similar or identical to right glenoid implant 100, although the left glenoid implant may be a substantially mirror image of the right glenoid implant 100. FIG. 1 is a perspective view of a lateral portion of the glenoid implant 100, while FIG. 2 is a perspective view of a medial portion of the glenoid implant 100. Generally, glenoid implant 100 may include an insert or an articulating portion 200 adapted to articulate with respect to a native or prosthetic humeral head, a base 10 adapted to contact the glenoid and to receive the articulating portion 200, and one or more fixation elements 300 such as screws to assist in fixing the base 10 to the glenoid.

FIGS. 2-10 illustrate various views of base 10. Base 10 may include a bone-facing surface 30 (best illustrated in FIGS. 5 and 7) and a second surface 20 opposite the bone-facing surface (best illustrated in FIGS. 3-4 and 6). The second surface 20 is intended for receiving or otherwise coupling to articulating portion 200, which in turn is intended to articulate with a corresponding humeral head of the shoulder joint, whether a native or prosthetic humeral head. In some embodiments, however, the second surface 20 may be adapted to directly articulate with the humeral head, without any additional intervening articulating portion. The bone-facing surface 30 is intended for facing toward the patient's glenoid upon implantation, although it should be understood that some portions of bone-facing surface 30 may be in contact with the patient's bone, while other portions may not be in contact with the patient's bone, as described in greater detail below. An augment portion 40 may extend generally medially from the bone-facing surface of base 10. For purpose of clarity, the bone-facing surface 30 faces medially when implanted, while the second surface 20 faces laterally when implanted. Referring back to FIGS. 3-4, the second surface 20 may include a plurality of apertures 50 extending between the medial and lateral faces of the second surface 20 for receiving fasteners 300 therethrough, such as bone screws, to help secure the base 10 to the patient's glenoid. The second surface 20 may also include a set screw aperture 60 extending between the medial and lateral faces of the second surface 20 for receiving a set screw 70 therethrough. In use, the set screw 70 may be advanced within the set screw aperture 60, and as the leading end of the set screw 70 pushes against the augment portion 40 while being advanced, the augment portion 40 may expand, bow outwardly (e.g. increase in convexity), or otherwise change shape, as is described in greater detail below.

With the general components of base 10 having been briefly described, these components, and a method of use of the glenoid implant 100, are described in greater detail below.

Figure 6:
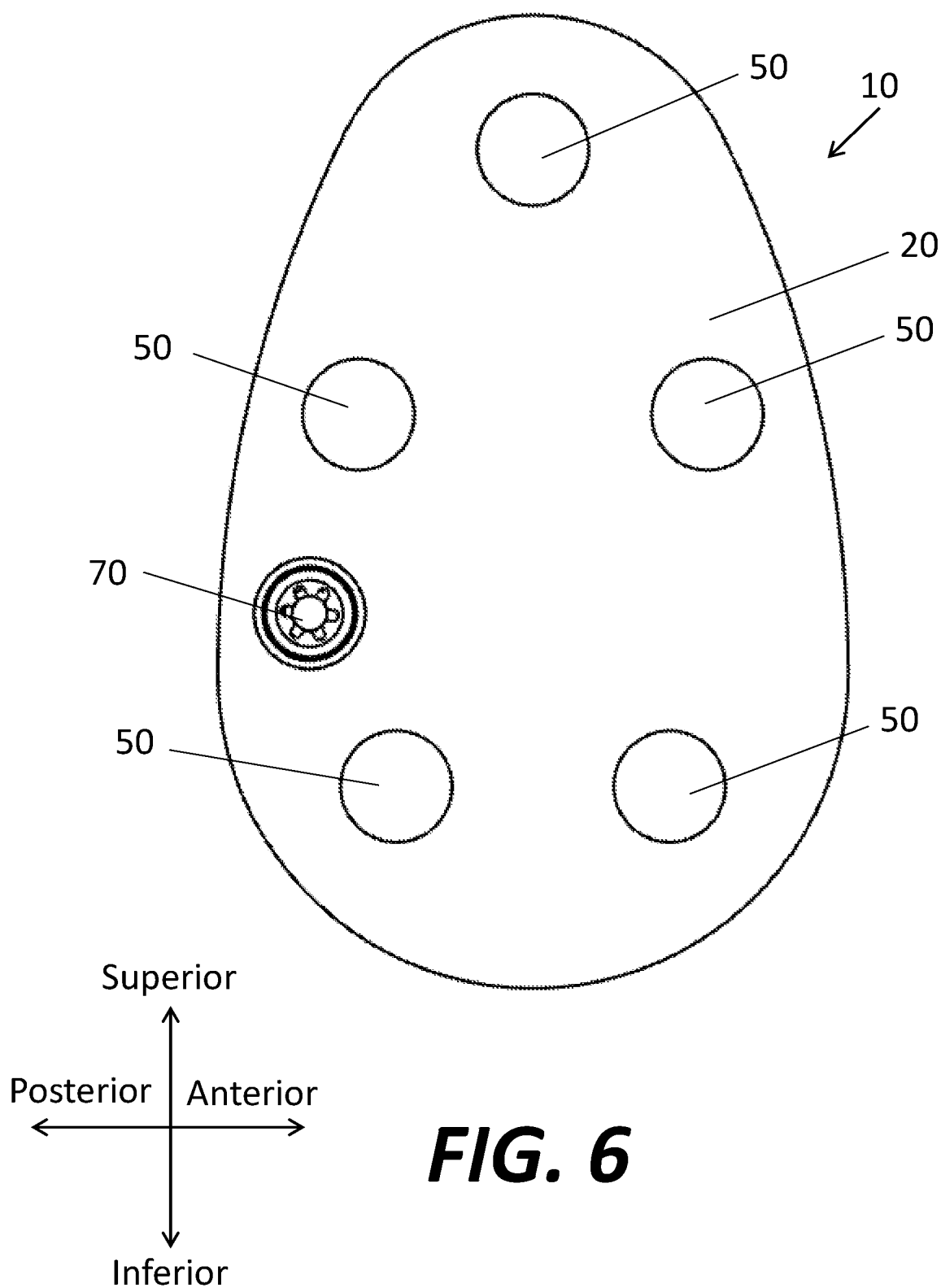
FIG. 6 is a plan view of a second surface of the base of FIG. 3.

Referring to FIG. 6, the second surface 20 of glenoid implant 10 may be generally ovoid or egg-shaped, with a relatively narrow superior end and a relatively wide inferior end, which may generally match the shape of a typical native glenoid and the shape of the articulating portion 200, although the articulating portion may have a larger perimeter than base 10. The second surface 20 may also have a concavity (best illustrated in FIGS. 3-4) that matches a concavity of articulation portion 200, which in turn is meant to assist in allowing the humeral head to articulate with respect to the glenoid implant 100. In the illustrated embodiment, second surface 20 includes a first superior aperture 50 substantially centered along the anterior-posterior direction of the base 10, a first pair of two apertures 50 on the anterior and posterior sides of the second surface 20 generally near a superior-inferior mid-point of the base 10, and a second pair of two apertures 50 on the inferior end of the second surface 20. One of the second pair of two apertures 50 may be closer to the posterior side of the base 10, while the other of the second pair of two apertures 50 may be closer to the anterior side of the base 10. With this one particular arrangement of apertures 50, a total of five apertures in an exaggerated pentagon shape may be provided, with each aperture 50 adapted to receive a fastener 300 therethrough to help secure the base 10 to the native glenoid. However, it should be understood that this arrangement of apertures is merely exemplary. Additional configurations of these apertures 50 may be provided without departing from the scope of the disclosure. For example, fewer than five apertures 50 may be provided, or more than five apertures 50 may be provided. Further, the apertures 50 may be positioned in different areas than those shown. However, it may be preferable to avoid having any apertures 50 that would align with the transition point between the paleoglenoid and neoglenoid of the patient, as it may be desirable to avoid placing a bone screw or other fastener 300 through that transition point. In the illustrated embodiment, all of the apertures 50 are generally adjacent an outer perimeter edge of the second surface 20. Preferably, the second surface 20 is formed of a biocompatible metal, such as titanium, although in some instances it may be suitable to form the second surface 20 from a biocompatible polymer or ceramic, such as any of those described below in connection with articulation surface 200. For example, if second surface 20 is being used to directly articulate with the humeral head, it may be preferable to form the second surface 20 of any such biocompatible polymer or ceramic.

Figure 5:
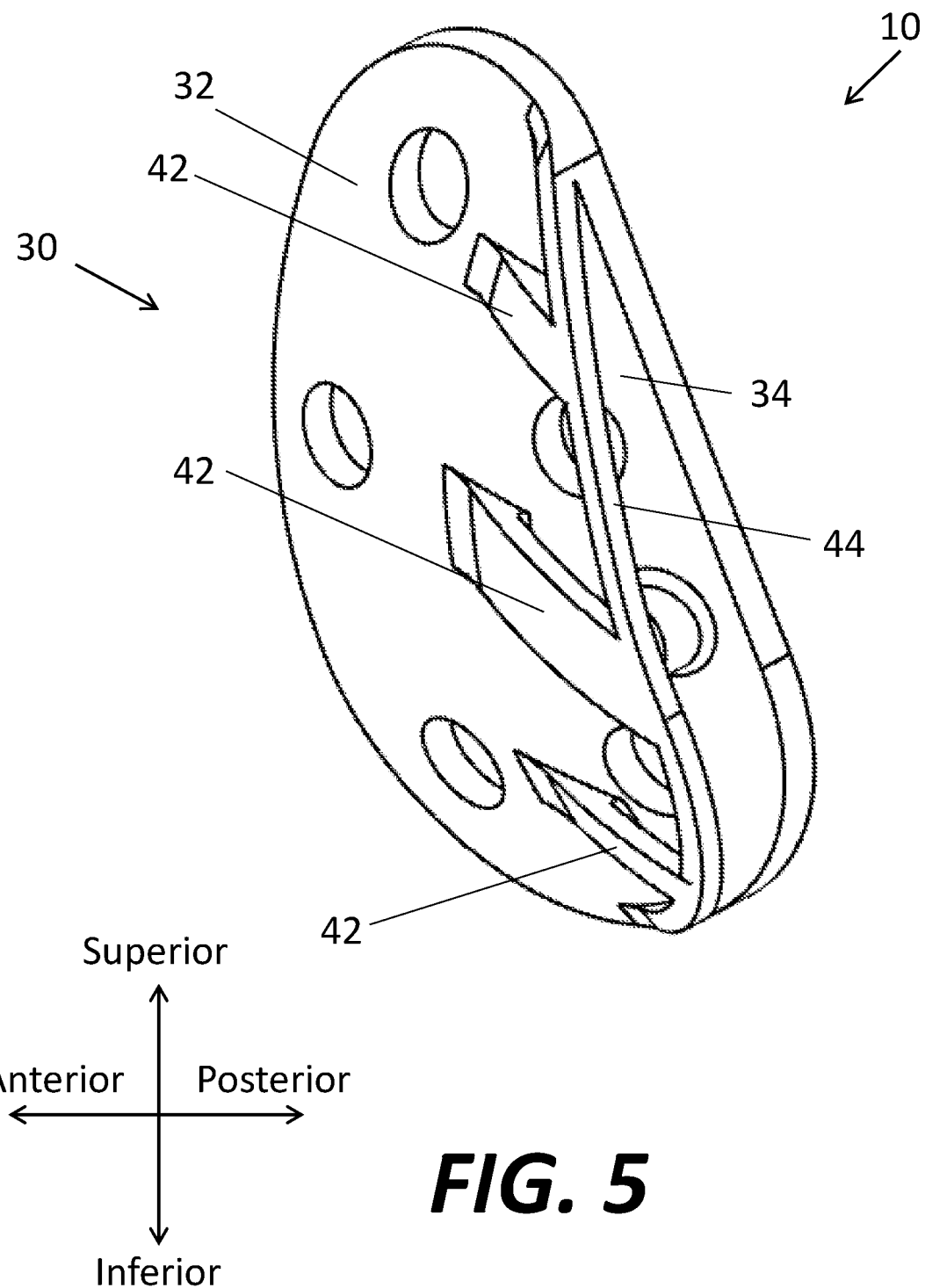
FIG. 5 is a perspective view of a bone-contacting surface of the base of FIG. 3.
Figure 7:
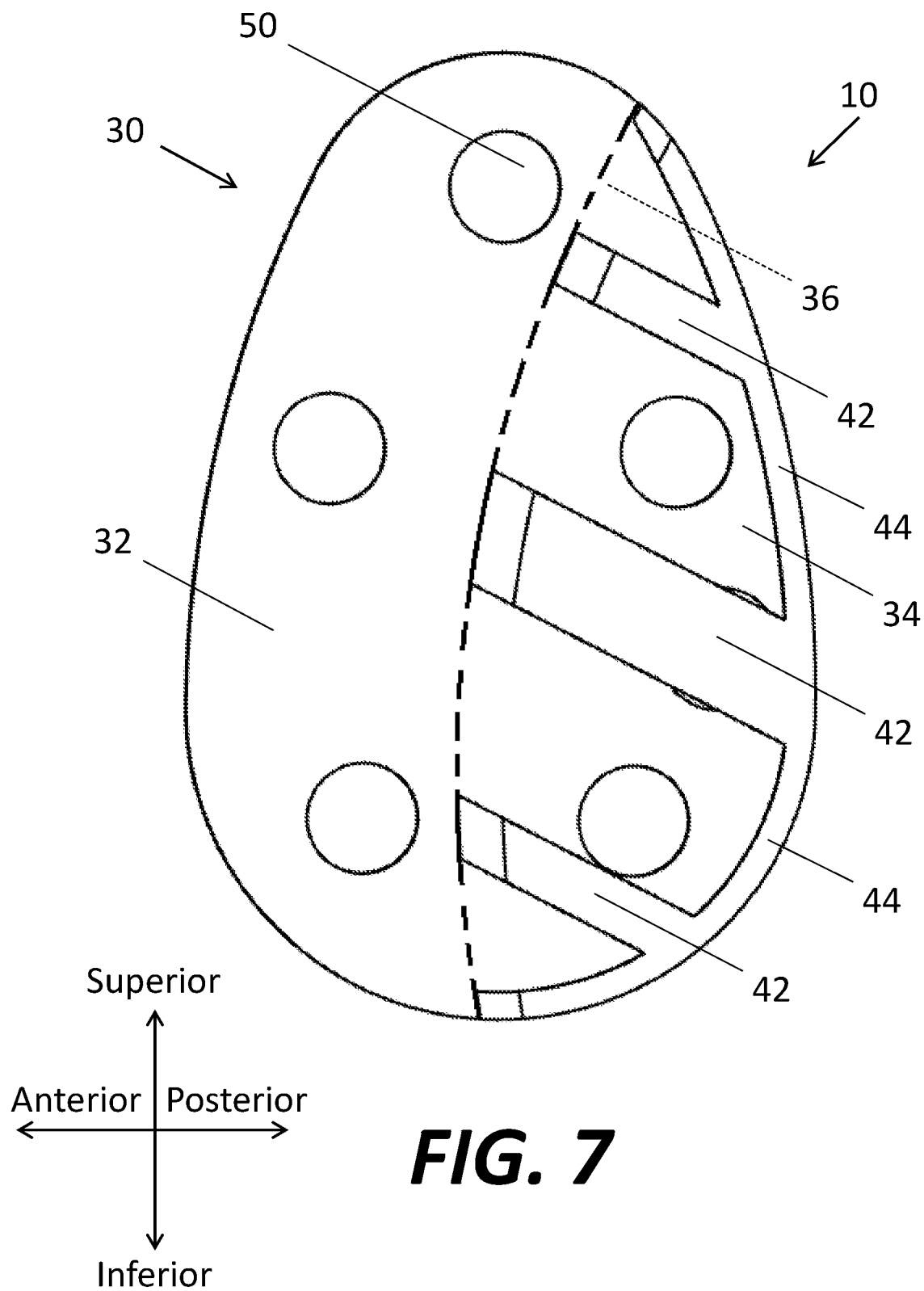
FIG. 7 is a plan view of the bone-contacting surface of the base of FIG. 3.

Referring now to FIGS. 5 and 7, the bone-facing surface 30 may have the same ovoid shape as the second surface 20, as the bone-facing surface 30 and the second surface 20 may be opposite sides of the same structure. However, whereas second surface 20 may have a concave surface, the bone-facing surface 30 preferably has as convex surface with a first convexity. As best shown in FIG. 7, the bone-facing surface 30 may be conceptually split into two components, including a first area 32 and a second area 34. An imaginary line 36 may be drawn along the beams 42 of the augment portion 40 (described in greater detail below) where the beams 42 couple to the bone-facing surface 30. This imaginary line 36 may effectively divide the bone-facing surface 30, with the first area 32 being intended to be in contact with bone, specifically the paleoglenoid, and the second area 34 intended to be spaced away from the bone via the augment portion 40. The trajectory of the imaginary line 36 may generally correspond to a typical trajectory of the line dividing the paleoglenoid from the neoglenoid in a native glenoid with eccentric glenoid erosion. The bone-facing surface 30 may also be made from a biocompatible metal, such as titanium. In some embodiments, the bone-facing surface 30 may include additional materials such as a porous metal, such as porous titanium, to increase bone ingrowth into the bone-facing surface 30, although such an additional feature is not necessary. In some embodiments, the second surface 20 and bone-facing surface 30 are two opposite faces of an integral structure that are spaced apart from one another by a thickness.

It should be understood that any of the apertures 50 that are positioned within the second area 34 of bone-facing surface 30, with the exception of the one or more set screw apertures 60, preferably have a longitudinal axis that extends between adjacent ones of the beams 42. On the other hand, the one or more set screw apertures 60 preferably have a longitudinal axis that aligns with a corresponding beam. With this configuration, any bone screws 300 that are used as fasteners through apertures 50 will avoid contacting the augment portion 40, while set screws 70 passing through set screw apertures 60 will contact the augment portion 40 to cause expansion of the augment portion 40, described in greater detail below.

Still referring to FIGS. 5 and 7, augment portion 40 may be coupled to bone-facing surface 30 of base 10. Generally, augment portion 40 has a skeletonized or truss-like frame that allows the augment portion 40 to be expanded and/or to bow outwardly and/or to change convexity. In one embodiment, the augment portion 40 includes a plurality of beams 42 spaced apart from one another having a first end coupled to the bone-facing surface 30. The second end of each beam 42 may be coupled to a rim 44 of the augment portion 40. The rim 44 may be relatively narrow or thin compared to one or more of the beams 42, and may have a contour that generally corresponds to a contour of the posterior perimeter of the bone-facing surface 30 of base 10. The beams 42 and/or rim 44 may have any suitable thickness, including for example between about 3 mm and about 7 mm. The rim 44 may be substantially continuous and connect the second ends of all of the beams 42. In the particular illustrated embodiment, three beams 42 connect the rim 44 to the bone-facing surface 30, with a central one of the beams 42 being wider or thicker than the peripheral beams 42 on either side of the central beam 42. The terminal ends of the rim 44 that couple to the bone-facing surface 30 may also be thought of as beams that are narrower than the other three beams 42, in which case base 10 may be thought of as having five beams. In any event, it should be understood that more or fewer beams 42 may be provided.

The augment portion 40 may be integrally formed with the bone-contacting surface 30, and may be formed of any desirable material including biocompatible metals, such as titanium. However, in other embodiments, the augment portion 40 may be formed separately from the remainder of base 10, and then coupled by any suitable fashion, including for example adhesives. In some instances, the augment portion 40 may be formed of a different material than the remainder of the base 10, such as a biocompatible polymer or ceramic, and in other cases the augment portion 40 may be formed of the same material as the remainder of the base 10. In some embodiments, the beams 42 may be omitted. For example, if the augment portion 40 is formed of metal, it may be preferable to include the beams 42 as shown to assist in the augment portion 40 changing shape. However, if the augment portion 40 is formed of a polymer or plastic, it may be preferable to remove beams 42, and instead only include rim 44 (including the two terminal ends of the rim 44 coupled to the bone-facing surface 30). Because a polymer or plastic may be significantly more flexible than typical metals, the augment portion 40 may suitably change shape and flex even if beams 42 are removed.

The first end of each beam 42 (and the terminal ends of the rim 44) may be movably coupled to the bone-contacting surface 30 to allow the second ends of the beams 42 (and the portions of rim 44 other than the terminal ends) to change position and/or shape relative to the bone-contacting surface 30. For example, in the illustrated embodiment, the first ends of each beam 42 (and the terminal ends of the rim 44) are hingedly coupled to the bone-contacting surface 30, such as via a living hinge. With this configuration, as briefly noted above, the augment portion 40 may be forced to expand as described in greater detail below.

Figure 8:
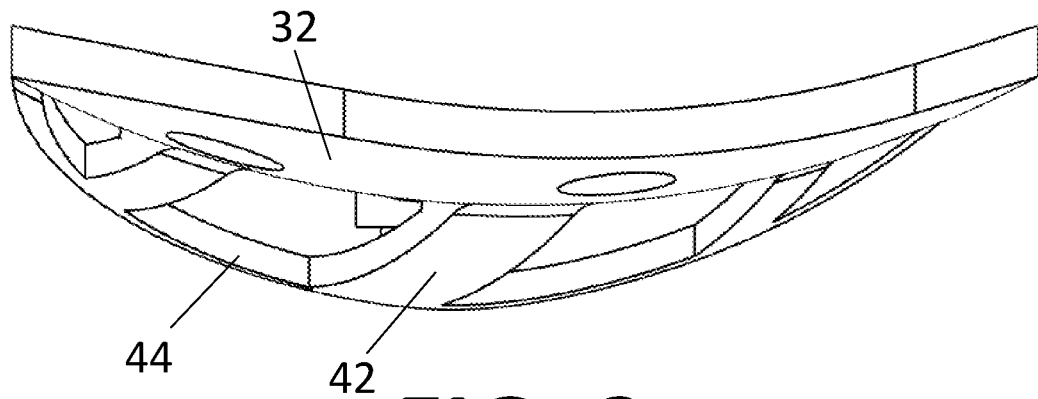
FIGS. 8-9 are side views of the base of FIG. 3.
Figure 9:
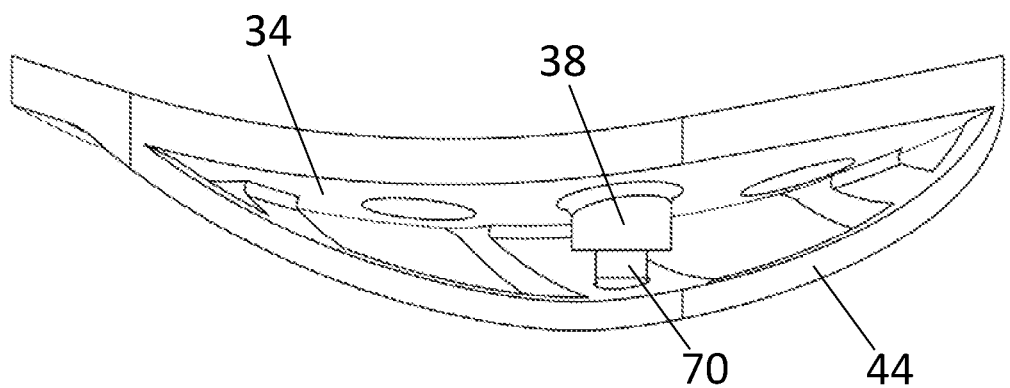
Figure 10:
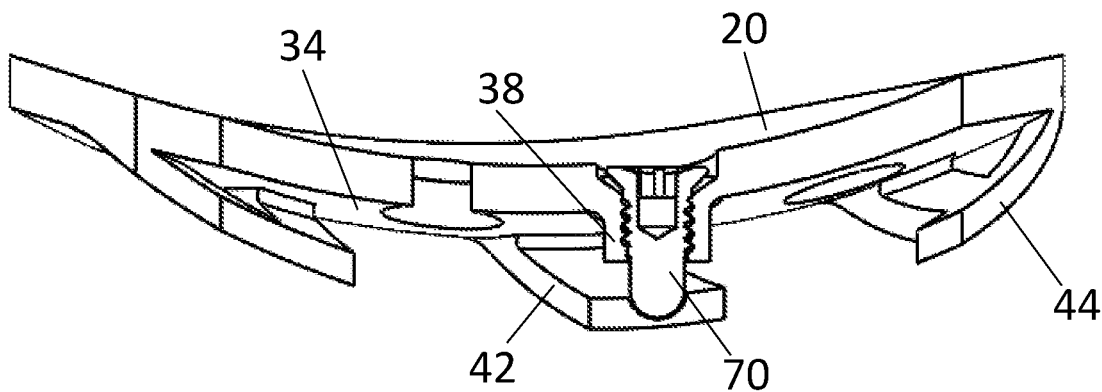
FIG. 10 is a cross-section of the base of FIG. 3.

FIGS. 8 and 9 illustrate anterior and posterior side views, respectively, of base 10, while FIG. 10 illustrates a cross-section of the base taken along a plane orthogonal to the medial-lateral direction, with a view of the posterior side of the base 10. FIGS. 8-10 all illustrate augment portion 40 having been extended or expanded via set screw 70. The set screw aperture 60 may include a general cylindrical extension 38 extending from the bone-facing surface 30 adjacent the set screw aperture 60 in a medial direction. A longitudinal axis of the set screw aperture 60 may be aligned with one of the beams 42, including the wider centrally located beam 42, as shown in FIGS. 9-10. The cylindrical extension 38 may include a mating feature such as threads, to assist in advancing the set screw 70 toward or away from the augment portion 40. In the illustrated embodiment, set screw 70 includes a shaft and a head. The shaft of set screw 70 may be entirely threaded, or partially threaded (e.g. a leading end may be unthreaded, and a trailing end adjacent the head may be threaded). As the set screw 70 is rotated to advance the set screw 70 through extension 38, a leading end or tip of the set screw 70 may contact one of the beams 42 (and/or portions of adjacent rim 44) to push the augment portion 40 away from the bone-facing surface 30. The head of set screw 70 and the set screw aperture 60 may be correspondingly shaped so that, when the set screw 70 is received within the set screw aperture 60, the head of the set screw 70 does not extend above the second surface 20 of the glenoid implant 10, so as to avoid disrupting coupling of the articulation portion 200 to the base 10, or in other embodiments where second surface 20 directly articulates with the humeral head, to avoid disrupting articulation between the humeral head and the second surface 20 of the base 10. Although the illustrated embodiment includes a single set screw 70, in other embodiments, additional set screws may be provided (along with additional set screw apertures) so that force may be applied on other ones of the beams 42 to further control the shape and contours of the augment portion 40.

Referring back to FIGS. 1-2, the articulating portion 200 may have a generally ovoid shape similar to that of base 10. Preferably, articulating portion 200 is formed of a biocompatible ceramic or polymer, such as polyethylene (including ultra-high molecular weight polyethylene) or polyether ether ketone ("PEEK"). Although not separately labeled, articulating portion 200 may include an articulating surface (shown in FIG. 1) intended to directly articulate with the humeral head of a patient, whether native or prosthetic. Articulating portion 200 may include a second surface opposite the articulating surface (shown in FIG. 2) that is adapted to face the glenoid and to couple to base 10. Any suitable coupling feature may be provided to couple the articulating portion 200 to the base 10. For example, articulating portion 200 may be snap-fit or press-fit onto the base 10. In other embodiments, the articulating portion 200 maybe coupled to the base 10 via adhesives, such as cement, or any other suitable modality. As shown in FIG. 2, the perimeter of articulating portion 200 may be slightly greater than that of base 10 so that there is some amount of overhang between the articulating portion 200 and the base 10, although in other embodiments the perimeters may be substantially the same. Further, as noted above, in some embodiments the articulation portion 200 may be omitted, and instead the second surface of the base 10 may be used to directly articulate with the humeral head. In such an embodiment, the base 10 may be formed of different materials so that the surface that articulates with the humeral head is formed of a polymer or ceramic, and the base 10 may be thicker than shown in the drawings.

In an exemplary method of using the glenoid implant 100, a patient's shoulder joint, and particularly the native glenoid, may be accessed by any suitable method. The patient's glenoid may require preparation prior to the implantation of implant 100. In some instances, a surgical robot with an associated cutting tool and/or an associated computer may be programmed to ream or otherwise prepare the surface(s) of the glenoid to accept glenoid implant 100. In other cases, any desired preparation of the glenoid may be performed manually, or via a combination of manual and automated and/or robotic tools.

In some embodiments, prior to preparing the glenoid, the set screw 70 may be advanced through set screw aperture 60 and the augment portion 40 expanded or re-configured to increase the convexity and/or the spacing of the rim 44 from the bone-facing surface 30, and the glenoid may be prepared to substantially match (or complement) the expanded configuration of the augment portion 40. However, in other embodiments, the augment portion 40 may be intraoperatively adjusted to match the glenoid surface (such as the prepared glenoid surface), with the set screw 70 allowing for fine-tuning of the shape of the augment portion 40 to best match the patient's glenoid.

In one example of such intraoperative adjustment, the base 10 may be placed against the native glenoid, with the first area 32 of the bone-facing surface 30 confronting the paleoglenoid, and the augment portion 40 confronting the neoglenoid. Depending on the fit, the set screw 70 may be advanced to expand or re-configure the shape and/or convexity of the augment portion 40 (also referred to as expanding the augment portion 40) until the augment portion 40 has a convexity and/or shape that suitably complements the concavity and/or shape of the neoglenoid. Such intraoperative adjustment may be performed prior to coupling the base 10 to the glenoid, or after partially coupling the base 10 to the glenoid. For example, the base 10 may be loosely placed against the glenoid (e g manually or with an associated holding tool) and the augment portion 40 may be expanded prior to fastening the base 10 to the bone with fasteners 300, such as bone screws. On the other hand, one or more fasteners 300, such as bone screws, may be placed through one or more of the apertures 50 and at least partially fastened (e.g. screwed) into the bone. With the one or more bone screws 300 holding the base 10 in place, the set screw 70 may be used to expand the augment portion 40 until the user is satisfied that the shape of the augment portion 40 desirably complements the shape of the neoglenoid. With the augment portion 40 configured in the desired shape, bone screws 300 that have already been fastened to the bone may be further secured and/or tightened, and/or additional bone screws may be used to fasten the base 10 to the bone through apertures 50 not already occupied by a bone screw 300. It should be understood that the set screw 70 is preferably coupled to the set screw aperture 60 and/or cylindrical extension 38 so that the set screw 70 will not change position relative to the base 10 as a result of normal forces, including normal use of the shoulder joint, or even via the forces resulting from bone screws 300 coupling the base 10 to the glenoid. As with the set screw 70, any fasteners 300 that pass through apertures 60 preferably do not protrude above the second surface 20 once in their final positions, so as to avoid interference with either the coupling of articulation portion 200, or with a humeral head articulating directly against the second surface 20. This may be achieved, similar to set screw aperture 60, by providing a countersink or other similar feature in the apertures 50. In some embodiments, one or more of the fasteners 300 may be locking screws, which may help reduce augment compression forces.

Although a single set screw 70 is described above as being adjusted to increase or decrease the amount of expansion or convexity of augment portion 40, it may be desirable to provide a plurality of set screws 70 of different lengths. By having available a plurality of set screws 70 of different lengths, it may be easier to achieve the desired level of expansion of augment portion 40 while minimizing the likelihood that the set screw 70 will protrude beyond the second surface 20 of base 10.

In an alternate but overall similar method of use, the first area 32 of base 10 may be coupled to the paleoglenoid of the patient via fasteners 300, although the fasteners may be less-than-fully tightened. The augment portion 40 may be adjusted to the desired size using set screw 70, and the articulation of the humeral head may be tested against the base 10 after attaching the articulation portion 200 to the base 10. If the size of the augment portion 40 needs to be adjusted, the articulation portion 200 may be removed, and the set screw 70 adjusted (or replaced with a different length set screw) to change the size and/or shape of the augment portion 40. Trialing may be completed again, and the process may be repeated until the size and/or shape of the augment portion 40 is satisfactory. When it is determined that the size and/or shape of the augment portion 40 is satisfactory, additional fasteners 300 may be inserted through the base 10 and into the neoglenoid, and any fasteners 300 already in the paleoglenoid may be further tightened if necessary. With all of the desired fasteners 300 coupling the base 10 to the glenoid, the articulation portion 200 may be coupled to the base 10, completing the implant procedure.

After finally securing the glenoid implant 100 in the desired position with the augment portion 40 having been adjusted to best fit the patient, the procedure may be completed, for example by closing the access that was previously created. In some embodiments, prior to closing the access, one or more bone graft materials and/or bone void filler materials may be placed to fill some of the open space between the augment portion 40 and the second area 34 of the bone-facing surface 30.

It should be clear that glenoid implant 100 allows for a single implant size to be used for a patients with a variety of anatomies. Whereas prior augmented glenoid implants may have included discrete implants of different sizes with the hope that one of the implant sizes would best fit a particular patient, glenoid implant 100, and particularly the base 10 thereof, is intraoperatively adjustable in infinitely small increments to provide a large range of sizes of the augment portion 40 to fit most or all patients. In other words, the first area 32 of bone-facing surface 30 may have a static shape and convexity, while the augment portion 40 may have a variable shape and convexity. For a patient with significant eccentric glenoid erosion resulting in a relatively "deep" neoglenoid, the augment portion 40 may be expanded to a relatively large amount to match that patient's particular anatomy. For a patient with less significant eccentric glenoid erosion that results in a relatively "shallow" neoglenoid, the augment portion 40 may not need to be expanded at all, or may only need to be minimally expanded, to match that patient's particular anatomy. As should be clear, a single design for glenoid implant 100 would allow for both patients to be treated, without the need for multiple glenoid implants being provided in a kit of different discrete sizes.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A glenoid implant for replacing a native glenoid, the glenoid implant comprising:
a concave articulating surface having a generally ovoid or egg-shape such that the articulating surface is configured to articulate with respect to a humeral head;
a bone-facing surface opposite the articulating surface, the bone-facing surface having a generally ovoid or egg-shape and further having a first area and a second area that collectively form the ovoid or egg-shape of the bone-facing surface, the first area being configured to contact a paleoglenoid of the native glenoid; and
an augment portion hingedly coupled to the bone-facing surface via a hinge, the augment portion being configured to contact a neoglenoid of the native glenoid while the first area contacts the paleoglenoid of the native glenoid, the augment portion being transitionable about the hinge between a first configuration in which the augment portion has a first convexity and a second configuration in which the augment portion has a second convexity different than the first convexity, a distance between the second area and the augment portion increasing upon the transitioning of the augment portion between the first configuration and the second configuration; and the augment portion includes a plurality of beams, each beam having a first end coupled to the bone-facing surface, and a second end coupled to a rim, the rim connecting the second ends of the beams.

2. The glenoid implant of claim 1, wherein the augment portion has a first end coupled to the bone-facing surface, and a second free end, the second free end being movable with respect to the bone-facing surface.

3. The glenoid implant of claim 1, wherein rim includes two terminal ends coupled to the bone-facing surface.

4. The glenoid implant of claim 1, wherein the plurality of beams includes three beams.

5. The glenoid implant of claim 1, wherein the rim has a contour that matches a contour of a posterior perimeter of the bone-facing surface.

6. The glenoid implant of claim 1, further comprising a plurality of fastener apertures in the bone-facing surface, each fastener aperture configured to receive a fastener therethrough.

7. The glenoid implant of claim 6, wherein at least one of the fastener apertures has a longitudinal axis that extends between two adjacent beams of the plurality of beams.

8. The glenoid implant of claim 1, further comprising a set screw aperture in the bone-facing surface, the set screw aperture configured to receive a set screw therethrough.

9. The glenoid implant of claim 8, wherein the set screw aperture has a longitudinal axis that aligns with a corresponding one of the plurality of beams.

10. The glenoid implant of claim 9, further comprising the set screw.

11. The glenoid implant of claim 10, wherein the set screw has threads, and the set screw aperture has corresponding threads.

12. The glenoid implant of claim 11, wherein the set screw is configured to be advanced through the set screw aperture so that a leading end of the set screw contacts the corresponding one of the plurality of beams.

13. The glenoid implant of claim 1, wherein the first ends of the plurality of beams are positioned along a transition line.

14. The glenoid implant of claim 13, wherein the second area is configured to be spaced away from the paleoglenoid of the native glenoid, the first area and the second area of the bone-facing surface being separated by the transition line.

15. The glenoid implant of claim 1, wherein the glenoid implant includes a base and an articulation portion adapted to couple to the base, the bone-facing surface being positioned on the base, and the articulating surface being positioned on the articulation portion.

16. The glenoid implant of claim 1, wherein the hinge is a living hinge.

* * * * *